United States Patent [19]
Tomoda

[11] Patent Number: 6,046,363
[45] Date of Patent: Apr. 4, 2000

[54] METHOD OF MAKING 4-HYDROXY-4'-BENZYLOXYDIPHENYL SULFONE

[75] Inventor: Yuichi Tomoda, Fukui, Japan

[73] Assignee: Nicca Chemical Co., Ltd., Fukui, Japan

[21] Appl. No.: 09/081,275

[22] Filed: May 20, 1998

[30] Foreign Application Priority Data

Dec. 24, 1997 [JP] Japan ..................................... 9-355360

[51] Int. Cl.[7] ................................................. C07C 315/00
[52] U.S. Cl. ................................................. 568/33; 568/32
[58] Field of Search ..................... 568/28, 33, 32

[56] References Cited

U.S. PATENT DOCUMENTS

| | | |
|---|---|---|
| 2,378,698 | 6/1945 | Gibbs . |
| 4,446,209 | 5/1984 | Iwakura . |
| 4,568,766 | 2/1986 | Yahagi ..................................... 568/33 |
| 4,616,239 | 10/1986 | Yagahi . |
| 5,284,978 | 2/1994 | Kinishi ..................................... 568/33 |
| 5,378,674 | 1/1995 | Kobayashi . |

FOREIGN PATENT DOCUMENTS

| | | |
|---|---|---|
| 465665 | 1/1992 | European Pat. Off. . |
| 251127 | 11/1987 | Germany . |
| 58-82788 | 5/1983 | Japan . |
| 59-225157 | 12/1984 | Japan . |
| 4210955 | 8/1992 | Japan . |
| 5117224 | 5/1993 | Japan . |
| 2112156 | 7/1983 | United Kingdom . |

OTHER PUBLICATIONS

World patent index accession No. 85–114288, abs of JP60056949, Aug. 9, 1993.
CA:109:190013 ab of CS246718, Jun. 6, 1984.
Schiff et al: Justus Liebigs Ann. Chem., vol. 221, 1883, pp. 365–379.
Chemical Abstracts, vol. 102, No. 25, Jun. 24, 1985, Abstract No. 220563.
Chemical Abstracts, vol. 109, No. 21, Nov. 21, 1988, Abstract.
Chemical Abstracts, vol. 111, No. 21, Nov. 20, 1989, Abstract No. 194211.

*Primary Examiner*—Gary Geist
*Assistant Examiner*—Jean F. Vollano
*Attorney, Agent, or Firm*—Leydig, Voit & Mayer, Ltd.

[57] ABSTRACT

The present invention provides a method of making 4-hydroxy-4'-benzyloxydiphenyl sulfone. The manufacturing method of the present invention is characterized in that an aqueous solvent containing an appropriate amount of a lower alcohol is used as a reaction solvent between 4,4'-dihydroxyphenyl sulfone and a benzyl halide.

20 Claims, No Drawings

METHOD OF MAKING 4-HYDROXY-4'-BENZYLOXYDIPHENYL SULFONE

BACKGROUND OF THE INVENTION

1. Field of the Invention

The present invention relates to a method of making 4-hydroxy-4'-benzyloxydiphenyl sulfone.

2. Related Background Art

It has been known that 4,4'-dihydroxydiphenyl sulfone-monobenzyl ether can be made when 4,4'-dihydroxydiphenyl sulfone(hereinafter abbreviated as BPS) and a benzyl halide (X—$CH_2C_6H_5$, where X indicates a halogen element) are reacted as materials in the presence of an alkali catalyst. As for its reaction solvent, both organic solvent system and aqueous solvent system have been known as well.

One of problems in such a method of making BPS-monobenzyl ether, in its industrial method in particular, is a problem of reaction selectivity in that 4,4'-dibenzyloxydiphenyl sulfone (hereinafter abbreviated as BPS-dibenzyl ether) is generated as a byproduct since BPS, which is a reaction material, has two phenolic hydroxyl groups. Such a problem of reaction selectivity results in difficulty in controlling reaction conditions, necessity for a step of isolating the product, and so forth. Another problem lies in the amount of solvent required for the reaction; it is preferably as small as possible from the viewpoint of the manufacturing apparatus, easiness in manufacturing condition control, manufacturing cost, and the like.

Japanese Patent Application Laid-Open No. 58-82788 discloses a manufacturing method in an organic solvent (dimethyl formamide) using BPS and benzyl chloride, in which an alkali metal carbonate is employed as a catalyst. This reaction is insufficient in terms of reaction selectivity, thus further necessitating a purification process by use of extraction or recrystallization. Japanese Patent Application Laid-Open No. 59-225157 and No. 4-210955 disclose a method of making BPS-monobenzyl ether comprising the steps of dissolving BPS by an alkali compound using water as a reaction solvent, further reacting benzyl chloride therewith, and isolating the resulting product. Japanese Patent Application Laid-Open No. 5-117224 discloses a manufacturing method in which, upon a reaction under a similar condition, an alkali compound is added to the aqueous reaction solution such that the latter attains a pH of 7.5 to 8.5. In such an aqueous solvent reaction system, a large amount of unreacted BPS would exist in the product mixture in order to restrain BPS-dibenzyl ether from occurring, thus necessitating a complicated purification process such as solvent extraction or recrystallization. Further, water as the solvent is necessary in an amount about 10 times that of BPS, thus making it problematic not only in that production per unit volume of the manufacturing apparatus is small but also in processing of such a large amount of waste solvent.

Accordingly, in a method of making BPS-monobenzyl ether, there has been a strong demand for a method having a high reaction selectivity, making a highly pure product without requiring a complicated purification process such as extraction or recrystallization, yielding a high quantity of production per unit volume of reaction solvent, and capable of minimizing the reaction waste liquid.

SUMMARY OF THE INVENTION

The present invention relates to a method of making 4-hydroxy-4'-benzyloxydiphenyl sulfone (hereinafter abbreviated as BPS-monobenzyl ether), which is a compound used as a photograph coupler material or a developer for thermal recording paper with favorable shelf stability, having the following general formula (1):

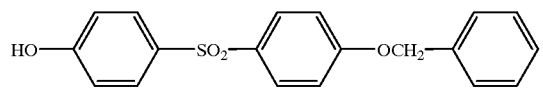

It is an object of the present invention to overcome the above-mentioned problems of the conventional methods of making BPS-monobenzyl ether, so as to provide a method having a high reaction selectivity, making a highly pure product without requiring a complicated purification process such as extraction or recrystallization, yielding a high quantity of production per unit volume of reaction solvent, and capable of minimizing the reaction waste liquid.

As a result of diligent studies in order to solve the above-mentioned problems, the inventors have found that the product per volume can be enhanced, while improving the reaction selectivity, when water is also used as a solvent upon reaction of a specific amount of lower alcohol. Based on this finding, the inventors have accomplished the present invention.

Namely, the present invention provides a method of making 4-hydroxy-4'-benzyloxydiphenyl sulfone by reacting 4,4'-dihydroxydiphenyl sulfone and a benzyl halide in the presence of an alkali catalyst, wherein water containing a lower alcohol is used as a solvent.

Also, the present invention provides the above-mentioned method of making 4-hydroxy-4'-benzyloxydiphenyl sulfone, wherein the above-mentioned lower alcohol is one member selected from the group consisting of methanol, ethanol, n-propanol, and isopropanol, or a mixture thereof.

Also, the present invention provides the above-mentioned method of making 4-hydroxy-4'-benzyloxydiphenyl sulfone, wherein the above-mentioned alkali catalyst is one member selected from the group consisting of sodium hydroxide, potassium hydroxide, lithium hydroxide, sodium carbonate, and potassium carbonate, or a mixture thereof.

Also, the present invention provides the above-mentioned method of making 4-hydroxy-4'-benzyloxydiphenyl sulfone, wherein the above-mentioned benzyl halide is one member selected from the group consisting of benzyl chloride, benzyl iodide, and benzyl bromide, or a mixture thereof.

Further, the present invention provides the above-mentioned method of making 4-hydroxy-4'-benzyloxydiphenyl sulfone, wherein the above-mentioned solvent is water containing 5% to 25% by weight of the above-mentioned lower alcohol.

Also, the present invention provides the above-mentioned method of making 4-hydroxy-4'-benzyloxydiphenyl sulfone, wherein 3 to 5 parts by weight of the above-mentioned solvent are used with respect to 1 part by weight of 4,4'-dihydroxydiphenyl sulfone.

Also, the present invention provides the above-mentioned method of making 4-hydroxy-4'-benzyloxydiphenyl sulfone, wherein 0.9 to 1.2 equivalents of the benzyl halide and 0.8 to 1.2 equivalents of the alkali catalyst are used with respect to 1 mole of 4,4'-dihydroxydiphenyl sulfone.

Further, the present invention provides the above-mentioned method of making 4-hydroxy-4'-benzyloxydiphenyl sulfone, further comprising a step of separating 4-hydroxy-4'-benzyloxydiphenyl sulfone by filtration from the reaction solution after completion of the reaction.

Namely, provided as a more specific embodiment of the present invention is a method of making 4-hydroxy-4'-benzyloxydiphenyl sulfone with a high purity obtained by adding 4,4'-dihydroxydiphenyl sulfone to 5% to 25% by weight of an aqueous lower alcohol solution in an amount which becomes 3 to 5 parts by weight with respect to 1 part by weight of 4,4'-dihydroxydiphenyl sulfone; adding 0.8 to 1.2 equivalents of a hydroxide and/or salt of an alkali metal with respect to 1 mole of 4,4'-dihydroxydiphenyl sulfone so as to dissolve the latter as a mono alkali metal salt of 4,4'-dihydroxydiphenyl sulfone; adding 0.9 to 1.2 equivalents of a benzyl halide thereto to effect a reaction; and, after the reaction, separating the slurry by filtration.

As a summary, since an aqueous solvent containing an appropriate amount of a lower alcohol is used as a reaction solvent, a very high reaction selectivity can be obtained, whereby the reaction product can be isolated with a high yield and a high purity by simply being filtered out, washed, and dried. Also, the amount of reaction solvent can be reduced, thus allowing the production per unit volume (of apparatus and solvent) to improve, the required manufacturing cost to cut down, and the required waste liquid processing to minimize. Then the method of making BPS-monobenzyl ether in accordance with the present invention is preferable as an industrial method of making 4-hydroxy-4'-benzyloxydiphenyl sulfone.

In the following, with reference to modes for carrying out the present invention, the method of making 4-hydroxy-4'-benzyloxydiphenyl sulfone in accordance with the present invention will be explained in detail.

DESCRIPTION OF THE PREFERRED EMBODIMENTS

Reaction Solvent

The method of making BPS-monobenzyl ether in accordance with the present invention uses water containing a lower alcohol as a reaction solvent in a method in which BPS and a benzyl halide ($X-CH_2C_6H_5$, where X indicates a halogen element) are reacted as materials in the presence of an alkali catalyst.

Though not restricted in particular, the lower alcohol used as the solvent together with water here is preferably an alcohol having 1 to 3 carbon atoms. As its specific examples, methanol, ethanol, n-propanol, and isopropanol may be listed.

Though not restricted in particular, the content (concentration) of such a lower alcohol is preferably 5% to 25% by weight (particularly preferably 5% to 15% by weight) with respect to water. Upon using a solvent in which the concentration of the lower alcohol is 25% by weight or more, the reaction selectivity tends to decrease, whereby unreacted BPS or BPS-dibenzyl ether is likely to occur as a byproduct. By contrast, when the concentration of the lower alcohol is not greater than 5% by weight, BPS tends to remain in a large amount.

Though not restricted in particular, the amount of the reaction solvent to be used in the present invention is preferably 3 to 5 parts by weight with respect to 1 part by weight of BPS. Namely, when this amount is not greater than 3 parts by weight with respect to BPS, the latter in the material is likely to remain in the reaction solvent without sufficiently dissolving, whereby BPS tends to remain unreacted even after the reaction, thus lowering the reaction selectivity and yield. By contrast, in the case where 5 parts by weight or more of the solvent are used with respect to 1 part by weight of BPS, the production per volume of reaction solvent would decrease, thus making it disadvantageous when the solvent is industrially treated in the reaction apparatus, reaction operation, separation processing, and so forth. Also, since a large amount of waste liquid is discharged, it becomes disadvantageous in terms of waste liquid processing.

Alkali Catalyst

Though not restricted in particular, a hydroxide or salt of an alkali metal is preferably usable as the alkali catalyst in the present invention. Specifically, sodium hydroxide, potassium hydroxide, lithium hydroxide, sodium carbonate, potassium carbonate, and the like may be listed, among which sodium hydroxide and potassium hydroxide are particularly preferable.

Though not restricted in particular, the amount of alkali catalyst to be used is preferably 0.8 to 1.2 equivalents with respect to 1 mole of BPS in the case of the above-mentioned hydroxide or salt of alkali metal. Here, since BPS has 2 hydroxyl groups, 1 equivalent refers to 1 mole of alkali catalyst calculated as hydroxyl group with respect to 1 mole of BPS. When the amount of alkali catalyst is not greater than 0.8 equivalent with respect to 1 mole of BPS, unreacted BPS tends to remain in a large amount; whereas, when it is used by 1.2 equivalents or more with respect to 1 mole of BPS, BPS-dibenzyl ether is likely to occur, thus lowering the reaction yield.

Also, while there is no particular restriction concerning the condition under which the alkali catalyst is added, it is preferably added after BPS is dissolved, so as to be dissolved as a monoalkali metal salt of BPS. When the reaction solvent of the present invention is used, the above-mentioned BPS exists substantially completely as a monoalkali metal salt in the solution.

Benzyl Halide

Though not restricted in particular, benzyl chloride (chloride), benzyl iodide (iodide), and benzyl bromide (bromide) are preferably usable as the benzyl halide in the present invention. Particularly preferable is benzyl chloride.

Though not restricted in particular, the amount of benzyl halide to be used is preferably 0.8 to 1.2 equivalents with respect to 1 mole of BPS. Here, since BPS has 2 hydroxyl groups, 1 equivalent refers to the amount of halide reacting with 1 hydroxyl group. When the amount of benzyl halide is not greater than 0.8 equivalent with respect to 1 mole of BPS, a large amount of BPS tends to remain unreacted in the reaction solution; whereas, when it is used by 1.2 equivalents or more with respect to 1 mole of BPS, BPS-dibenzyl ether is likely to occur as a byproduct.

Reaction Condition

Though not restricted in particular, the reaction temperature in the present invention is preferably within the range of 40° to 90° C., more preferably within the range of 50° to 70° C. At the early stage of reaction, the reaction material has preferably been dissolved, and temperature is preferably sufficient for dissolution. In general, at a temperature of 50° C. or lower, the material or part of the product is deposited as a solid before reaction. Even in this case, the reaction may be started from a slurry state. By contrast, at a temperature of 90° C. or higher, the reaction selectivity tends to decrease, whereby BPS-dibenzyl ether is likely to occur as a byproduct.

In the present invention, there is no particular restriction concerning preferable reaction time, which can be optimized as the progress of reaction is monitored. Preferably, after the benzyl halide is added, the reaction is sufficiently pursued at the same temperature as it is. For example, when part of the reaction mixture is taken out and is subjected to such known means as high-performance liquid chromatography, thinlayer chromatography, gas chromatography, or the like, the material or product can be monitored rapidly, thus allowing the time required for the reaction to be determined.

Under the manufacturing condition in accordance with the present invention explained above, when the reaction mixture liquid that has completed the reaction is cooled to a temperature of about 20° to 40° C., BPS-monobenzyl ether, which is the product, is deposited as a crystal. In this case, byproducts and unreacted material tend to coexist with the product when cooling temperature is lower than 20° C. At a higher temperature, by contrast, yield tends to decrease, though purity increases. Accordingly, an appropriate cooling temperature can be set in view of yield and purity. In general, through filtration at a temperature of 20° to 60° C., unreacted BPS transfers to the filtrate, whereby BPS-monobenzyl ether is obtained with a high purity (at least 96%) and a high yield (at least 80%).

The purity of BPS-monobenzyl ether obtained by filtration under the above-mentioned condition can be confirmed by known analyzing means. Specifically, various methods in which, while a reaction product obtained by a reaction in a usual operation is separated and purified, as a standard, with a chloroform solvent by use of a silica gel column, BPS-monobenzyl ether obtained is subjected to high-performance liquid chromatography (e.g., Type LC-10 manufactured by Shimadzu Corp.), gas chromatography (e.g., Type GC-16A manufactured by Shimadzu Corp.), nuclear magnetic resonance spectrometer (e.g., Type R-90H manufactured by Hitachi Ltd.), infrared absorption spectrometer (1600 FTIR manufactured by Perkin-Elmer Corp.), elementary analysis (2400 CHN Elemental Analyzer manufactured by Perkin-Elmer Corp.), and the like can be used preferably. Further, the melting point of obtained BPS-monobenzyl ether can be measured by a thermal-flux differential scanning calorimeter (e.g., Type DSC-50 manufactured by Shimadzu Corp.) or the like.

Detectable as the byproducts generated by the manufacturing method in accordance with the present invention or coexisting impurities are not only unreacted BPS and the dibenzyl ether of BPS, but also a benzyl ether, $C_6H_5CH_2OR$, which is a reaction product between the benzyl halide and lower alcohol. Here, R is the alkyl group of the lower alcohol ROH used for the reaction. Specifically, it is benzyl methyl ether when methyl alcohol is used, whereas it is isopropylbenzyl ether when isopropyl alcohol is used. Such a byproduct is specific to the method in accordance with the present invention, and it can be detected by various kinds of known organic trace analyzing methods. Specifically, gas chromatography, mass spectrometry, high-performance liquid chromatography, and the like can be used.

Further, the manufacturing method in accordance with the present invention is characterized in that the reaction waste liquid contains not only water but also a predetermined amount of lower alcohol. Accordingly, when part of the reaction waste liquid is subjected to usual organic analyzing means, whether a predetermined amount of lower alcohol exists or not can be confirmed. Specifically, the waste liquid can be analyzed by gas chromatography, mass spectrometry, high-performance liquid chromatography, and the like.

EXAMPLE

In the following, the present invention will be explained in detail with reference to examples, which by no means restrict the present invention.

Example 1

BPS (250 g, 1.0 mole) and sodium hydroxide (40 g, 1.0 mole) were dissolved in 1250 g of an aqueous solution containing 5% by weight of methanol, and benzyl chloride (126.6 g, 1.0 mole) was added dropwise thereto for 4 hours at 60° C. After the dropwise addition was completed, the reaction was further pursued at 60° C. for 6 hours. After the reaction was completed, the reaction solution was cooled to 35° C., and the purified product deposited thereupon was isolated by filtration. After being washed with water several times, the isolated product was dried under reduced pressure (yield after drying: 290.7 g, yield from BPS: 85.5%).

Thus obtained crystal was found to be BPS-monobenzyl ether having a purity of 97.4% according to high-performance liquid chromatography (column: Shim-pack CLC-ODS, eluting solvent: 65% aqueous acetonitrile solution, standard: BPS-monobenzyl ether having a purity of 99.9% obtained by the above-mentioned technique). Further, as a byproduct, BPS-dibenzyl ether (0.8%) was found in the above-mentioned high-performance liquid chromatography. The melting point of the product was 164° C. (as measured by a thermal-flux differential scanning calorimeter).

Example 2

BPS (250 g, 1.0 mole) and sodium hydroxide (40 g, 1.0 mole) were dissolved in 750 g of an aqueous solution containing 20% by weight of methanol, and benzyl chloride (126.6 g, 1.0 mole) was added dropwise thereto for 4 hours at 75° C. After the dropwise addition was completed, the reaction was further pursued at 75° C. for 6 hours. After the reaction was completed, the reaction solution was cooled to 35° C., and the purified product deposited thereupon was isolated by filtration. After being washed with water several times, the isolated product was dried under reduced pressure (yield after drying: 286.3 g, yield from BPS: 84.2%).

Thus obtained crystal was found to be BPS-monobenzyl ether having a purity of 96.9% according to high-performance liquid chromatography (conducted under the same condition as that of Example 1). Further, as a byproduct, BPS-dibenzyl ether (1.0%) was found in the above-mentioned high-performance liquid chromatography. The melting point of the product was 163° C. (as measured by a thermal-flux differential scanning calorimeter).

Example 3

BPS (250 g, 1.0 mole) and sodium hydroxide (40 g, 1.0 mole) were dissolved in 1250 g of an aqueous solution containing 5% by weight of isopropanol, and benzyl chloride (126.6 g, 1.0 mole) was added dropwise thereto for 4 hours at 60° C. After the dropwise addition was completed, the reaction was further pursued at 60° C. for 6 hours. After the reaction was completed, the reaction solution was cooled to 35° C., and the purified product deposited thereupon was isolated by filtration. After being washed with water several times, the isolated product was dried under reduced pressure (yield after drying: 273.4 g, yield from BPS: 80.4%).

Thus obtained crystal was found to be BPS-monobenzyl ether having a purity of 96.3% according to high-performance liquid chromatography (conducted under the same condition as that of Example 1). Further, as a byproduct, BPS-dibenzyl ether (1.2%) was found in the above-mentioned high-performance liquid chromatography. The melting point of the product was 161° C. (as measured by a thermal-flux differential scanning calorimeter).

Comparative Example 1

BPS (250 g, 1.0 mole) and sodium hydroxide (40 g, 1.0 mole) were dissolved in 2500 g of water, and benzyl chloride (126.6 g, 1.0 mole) was added dropwise thereto for 4 hours at 60° C. After the dropwise addition was completed, the reaction was further pursued at 60° C. for 6 hours. After the reaction was completed, the reaction solution was cooled to 35° C., and the purified product deposited thereupon was isolated by filtration. After being washed with water several times, the isolated product was dried under reduced pressure (yield after drying: 286.6 g, yield from BPS: 84.3%).

Thus obtained crystal was found to be BPS-monobenzyl ether having a purity of 90.9% according to high-performance liquid chromatography (conducted under the same condition as that of Example 1). Further, as a byproduct, BPS-dibenzyl ether (5.7%) was found in the above-mentioned high-performance liquid chromatography. The melting point of the product was 154° C. (as measured by a thermal-flux differential scanning calorimeter).

Comparative Example 2

BPS (250 g, 1.0 mole) and sodium hydroxide (40 g, 1.0 mole) were dissolved in 1250 g of water, and benzyl chloride (126.6 g, 1.0 mole) was added dropwise thereto for 4 hours at 80° C. After the dropwise addition was completed, the reaction was further pursued at 80° C. for 6 hours. After the reaction was completed, the reaction solution was cooled to 35° C., and the purified product deposited thereupon was isolated by filtration. After being washed with water several times, the isolated product was dried under reduced pressure (yield after drying: 306.7 g, yield from BPS: 90.2%).

Thus obtained crystal was found to be BPS-monobenzyl ether having a purity of 88.4% according to high-performance liquid chromatography (conducted under the same condition as that of Example 1). Further, as a byproduct, BPS-dibenzyl ether (6.8%) was found in the above-mentioned high-performance liquid chromatography. The melting point of the product was 153° C. (as measured by a thermal-flux differential scanning calorimeter).

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method of making 4-hydroxy-4'-benzyloxydiphenyl sulfone comprising reacting 4,4'-dihydroxydiphenyl sulfone and a benzyl halide in the presence of an alkali metal base catalyst, and in a solvent comprising water and a lower alcohol, wherein said lower alcohol is present in an amount of from 5% to 25% by weight of said solvent.

2. A method according to claim 1, wherein said lower alcohol is one member selected from the group consisting of methanol, ethanol, n-propanol, and isopropanol, or a mixture thereof.

3. A method according to claim 1, wherein said alkali metal base catalyst is one member selected from the group consisting of sodium hydroxide, potassium hydroxide, lithium hydroxide, sodium carbonate, and potassium carbonate, or a mixture thereof.

4. A method according to claim 1, wherein said benzyl halide is one member selected from the group consisting of benzyl chloride, benzyl iodide, and benzyl bromide, or a mixture thereof.

5. A method according to claim 1, wherein 3 to 5 parts by weight of said solvent are used with respect to 1 part by weight of 4,4'-dihydroxydiphenyl sulfone.

6. A method according to claim 1, wherein 0.9 to 1.2 equivalents of said benzyl halide and 0.8 to 1.2 equivalents of said alkali catalyst are used with respect to 1 mole of 4,4'-dihydroxydiphenyl sulfone.

7. A method according to claim 2, wherein 0.9 to 1.2 equivalents of said benzyl halide and 0.8 to 1.2 equivalents of said alkali metal base catalyst are used with respect to 1 mole of 4,4'-dihydroxydiphenyl sulfone.

8. A method according to claim 3, wherein 0.9 to 1.2 equivalents of said benzyl halide and 0.8 to 1.2 equivalents of said alkali metal base catalyst are used with respect to 1 mole of 4,4'-dihydroxydiphenyl sulfone.

9. A method according to claim 4, wherein 0.9 to 1.2 equivalents of said benzyl halide and 0.8 to 1.2 equivalents of said alkali metal base catalyst are used with respect to 1 mole of 4,4'-dihydroxydiphenyl sulfone.

10. A method according to claim 6, wherein 0.9 to 1.2 equivalents of said benzyl halide and 0.8 to 1.2 equivalents of said alkali metal base catalyst are used with respect to 1 mole of 4,4'-dihydroxydiphenyl sulfone.

11. A method according to claim 1, further comprising a step of separating 4-hydroxy-4'-benzyloxydiphenyl sulfone by filtering 4-hydroxy-4'-benzyloxydiphenyl sulfone after completion of said reaction.

12. A method according to claim 2, further comprising a step of separating 4-hydroxy-4'-benzyloxydiphenyl sulfone by filtering 4-hydroxy-4'-benzyloxydiphenyl sulfone after completion of said reaction.

13. A method according to claim 3, further comprising a step of separating 4-hydroxy-4'-benzyloxydiphenyl sulfone by filtering 4-hydroxy-4'-benzyloxydiphenyl sulfone after completion of said reaction.

14. A method according to claim 4, further comprising a step of separating 4-hydroxy-4'-benzyloxydiphenyl sulfone by filtering 4-hydroxy-4'-benzyloxydiphenyl sulfone after completion of said reaction.

15. A method according to claim 5, further comprising a step of separating 4-hydroxy-4'-benzyloxydiphenyl sulfone by filtering 4-hydroxy-4'-benzyloxydiphenyl sulfone after completion of said reaction.

16. A method according to claim 6, further comprising a step of separating 4-hydroxy-4'-benzyloxydiphenyl sulfone by filtering 4-hydroxy-4'-benzyloxydiphenyl sulfone from after completion of said reaction.

17. A method according to claim 7, further comprising a step of separating 4-hydroxy-4'-benzyloxydiphenyl sulfone by filtering 4-hydroxy-4'-benzyloxydiphenyl sulfone after completion of said reaction.

18. A method according to claim 8, further comprising a step of separating 4-hydroxy-4'-benzyloxydiphenyl sulfone by filtering 4-hydroxy-4'-benzyloxydiphenyl sulfone after completion of said reaction.

19. A method according to claim 9, further comprising a step of separating 4-hydroxy-4'-benzyloxydiphenyl sulfone by filtering 4-hydroxy-4'-benzyloxydiphenyl sulfone after completion of said reaction.

20. A method according to claim 10, further comprising a step of separating 4-hydroxy-4'-benzyloxydiphenyl sulfone by filtering 4-hydroxy-4'-benzyloxydiphenyl sulfone after completion of said reaction.

* * * * *